United States Patent [19]

Trivette, Jr. et al.

[11] 3,969,349
[45] July 13, 1976

[54] VULCANIZATION OF RUBBER WITH PHOSPHORO TRIAZINE SULFIDES

[75] Inventors: Chester D. Trivette, Jr.; Otto W. Maender, both of Akron, Ohio

[73] Assignee: Monsanto Company, St. Louis, Mo.

[22] Filed: Jan. 8, 1975

[21] Appl. No.: 539,266

Related U.S. Application Data

[62] Division of Ser. No. 421,126, Dec. 3, 1973, Pat. No. 3,867,358.

[52] U.S. Cl. .................. 260/247.1 M; 260/248 CS; 260/249.5; 260/249.8; 260/243 B; 260/79.5 C
[51] Int. Cl.² ...................................... C07D 251/38
[58] Field of Search ........ 260/248 CS, 249.5, 249.8, 260/247.1 M, 243 B

[56] References Cited

UNITED STATES PATENTS

3,261,834  7/1966  Imel et al. .......................... 260/248
3,366,598  1/1968  Westlinning et al. ............ 260/248 X Primary Examiner—John M. Ford

[57] ABSTRACT

Triazine sulfides of the formula

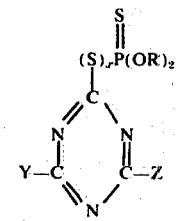

in which Y is

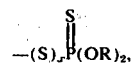

or

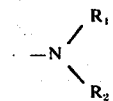

and Z is

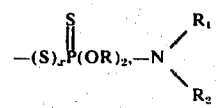

or Cl, are improved accelerators and vulcanizing agents for the vulcanization of rubber.

10 Claims, No Drawings

VULCANIZATION OF RUBBER WITH PHOSPHORO TRIAZINE SULFIDES

This application is a division of Ser. No. 421,126 filed Dec. 3, 1973 now U.S. Pat. No. 3,867,358 issued Feb. 18, 1975.

BACKGROUND OF THE INVENTION

This invention concerns a class of triazine compounds which are useful as vulcanizing and accelerating agents in the vulcanization of rubber. More particularly, it concerns s-triazine sulfides derived from dithiophosphoric acids.

SUMMARY OF THE INVENTION

It has been discovered that phosphorothioic acid triazine sulfides are excellent vulcanizing and accelerating agents for the vulcanization of rubber. Rubber compositions containing the sulfides exhibit improved processing safety and fast cure rates and produce strong vulcanizates. According to this invention an improved class of vulcanizing agents and accelerators for rubber are characterized by the formula

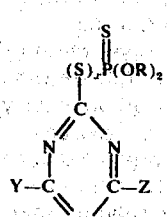

in which Y is

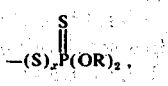

or

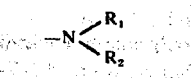

and Z is

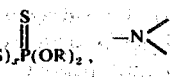

or Cl in which each R independently is alkyl of 1–8 carbon atoms, cycloalkyl of 5–8 carbon atoms, benzyl, phenyl or tolyl, $x$ is 1 or 2, and $R_1$ and $R_2$ independently are hydrogen, alkyl of 1–8 carbon atoms, cycloalkyl of 5–8 carbon atoms, benzyl, phenyl or tolyl or $R_1$ and $R_2$ together with the nitrogen atom form a heterocycle of 4–8 carbon atoms which heterocycle may be interrupted by oxygen or sulfur.

Preferably, Y is

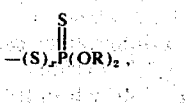

and Z is

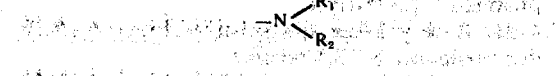

or both Y and Z are

and a further preferred sub group is when $x$ is two.

Branched and unbranched alkyl radicals are suitable for the practice of the invention with lower alkyl radicals of 1–4 carbon atoms being preferred. Illustrative examples are methyl, ethyl, propyl, isopropyl, butyl, isobutyl, sec.-butyl, tert-butyl, amyl, hexyl, heptyl, octyl and tert-octyl. Illustrative examples of cycloalkyl radicals are cyclopentyl, cyclohexyl, 4-methylcyclohexyl, 2-methylcyclohexyl, and cyclooctyl with cyclohexyl being preferred.

Monocyclic six membered ring amino radicals formed by $R_1$ and $R_2$ along with the nitrogen atom is a preferred heterocyclic subclass, however, monocyclic and bicyclic five to nine membered amino radicals are suitable. Illustrative examples of heterocyclic amino radicals are pyrrolidinyl, 2,5-dimethylpyrrolidinyl, piperidino, 4-methylpiperidino, morpholino, thiomorpholino, 2,6-dimethylmorpholino, hexahydro-1H-azepin-1-yl, hexahydro-1(2H)-azocin-1-yl, and azabicyclo(3.2.2)non-3-yl.

Illustrative compounds of this invention are:
2,4-di(0,0'-dimethylphosphorotrithioyl)-6-(N,N-dimethylamino)-1,3,5-triazine
2,4-di(0,0'-dimethylphosphorotrithioyl)-6-(N,N-diethylamino)-1,3,5-triazine
2,4-di(0,0'-dimethylphosphorotrithioyl)-6-(N,N-diisopropylamino)-1,3,5-triazine
2,4-di(0,0'-dimethylphosphorotrithioyl)-6-(N,N-dibutylamino)-1,3,5-triazine
2,4-di(0,0'-dimethylphosphorotrithioyl)-6-(N,N-dibenzylamino)-1,3,5-triazine
2,4-di(0,0'-dimethylphosphorotrithioyl)-6-(piperidino)-1,3,5-triazine
2,4-di(0,0'-dimethylphosphorotrithioyl)-6-(,2,6 dimethylmorpholino)-1,3,5-triazine
2,4-di(0,0'-dimethylphosphorotrithioyl)-6-(hexahydro-1H-azepin-1-yl)-1,3,5-triazine
2,4-di(0,0'-diisopropylphosphorotrithioyl)-6-(N,N-dimethylamino)-1,3,5-triazine
2,4-di(0,0'-diisopropylphosphorotrithioyl)-6-(N,N-dipropylamino)-1,3,5-triazine
2,4-di(0,0'-diisopropylphosphorotrithioyl)-6-(N,N-dihexylamino)-1,3,5-triazine
2,4-di(0,0'-diisopropylphosphorotrithioyl)-6-(N-ethyl-N-cyclohexylamino)-1,3,5-triazine
2,4-di(0,0'-diisopropylphosphorotrithioyl)-6-(pyrrolidinyl)-1,3,5-triazine
2,4-di(0,0'-diisopropylphosphorotrithioyl)-6-(4-methylpiperidino)-1,3,5-triazine
2,4-di(0,0'-dibenzylphosphorotrithioyl)-6-(N,N-dimethylamino)-1,3,5-triazine
2,4-di(0,0'-dibenzylphosphorotrithioyl)-6-(N,N-diethylamino)-1,3,5-triazine
2,4-di(0,0'-dibenzylphosphorotrithioyl)-6-(N,N-diisopropylamino)-1,3,5-triazine
2,4-di(0,0'-dibenzylphosphorotrithioyl)-6-(N,N-dicyclohexylamino)-1,3,5-triazine 2,4-di(0,0'-dibenzylphosphorotrithioyl)-6-(morpholino)-1,3,5-triazine
2,4-di(0,0'-dicyclohexylphosphorotrithioyl)-6-(N,N-dimethylamino)-1,3,5-triazine
2,4-di(0,0'-dicyclohexylphosphorotrithioyl)-6-(N,N-dipropylamino)-1,3,5-triazine
2,4-di(0,0'-dicyclohexylphosphorotrithioyl)-6-(N,N-dibutylamino)-1,3,5-triazine
2,4-di(0,0'-dicyclohexylphosphorotrithioyl)-6-(2,5dimethylpyrrolidinyl)-1,3,5-triazine
2,4-di(0,0'-dicyclohexylphosphorotrithioyl)-6-(2,6-dimethylmorpholino)-1,3,5-triazine
2,4-di(0,0'-dicyclohexylphosphorotrithioyl)-6-(N,N-dibenzylamino)-1,3,5-triazine
2,4-di(0,0'-dicyclohexylphosphorotrithioyl)-6-(hexahydro-1(2H)-azocin-1-yl)-1,3,5-triazine
2,4-di(0,0'-diethylphosphorotrithioyl)-6-(N,N-dimethylamino)-1,3,5-triazine
2,4-di(0,0'-diethylphosphorotrithioyl)-6-(N,N-dibutylamino)-1,3,5-triazine
2,4-di(0,0'-diethylphosphorotrithioyl)-6-(N-methyl-N-cyclohexylamino)-1,3,5-triazine
2,4-di(0,0'-diethylphosphorotrithioyl)-6-[N,N-di(2-ethylhexylamino)]-1,3,5-triazine
2,4-di(0,0'-diethylphosphorotrithioyl)-6-(N,N-dibenzylamino)-1,3,5-triazine
2,4-di(0,0'-diethylphosphorotrithioyl)-6-(pyrrolidinyl)-1,3,5-triazine
2,4-di(0,0'-diethylphosphorotrithioyl)-6-(piperidino)-1,3,5-triazine
2,4-di(0,0'-diethylphosphorotrithioyl)-6-(morpholino)-1,3,5-triazine
2,4-di(0-methyl-0'-phenylphosphorotrithioyl)-6-(N,N-dimethylamino)-1,3,5-triazine
2,4-di(0-methyl-0'-phenylphosphorotrithioyl)-6-(N,N-diethylamino)-1,3,5-triazine
2,4-di(0-methyl-0'-phenylphosphorotrithioyl)-6-(N,N-dipropylamino)-1,3,5-triazine
2,4-di(0-methyl-0'-phenylphosphorotrithioyl)-6-(N,N-dibutylamino)-1,3,5-triazine
2,4-di(0-methyl-0'-phenylphosphorotrithioyl)-6-(N,N-dibenzylamino)-1,3,5-triazine
2,4-di(0-methyl-0'-phenylphosphorotrithioyl)-6-(N,N-dicyclohexylamino)-1,3,5-triazine
2,4-di(0,0'-dimethylphosphorotrithioyl)-6-(N-methylamino)-1,3,5-triazine
2,4-di(0,0'-dimethylphosphorotrithioyl)-6-(N-ethylamino)-1,3,5-triazine
2,4-di(0,0'-dimethylphosphorotrithioyl)-6-(N-isopropylamino)-1,3,5-triazine
2,4-di(0,0'-dimethylphosphorotrithioyl)-6-(N-butylamino)-1,3,5-triazine
2,4-di(0,0'-dimethylphosphorotrithioyl)-6-(N-benzylamino)-1,3,5-triazine
2,4-di(0,0'-dimethylphosphorotrithioyl)-6-(N-phenylamino)-1,3,5-triazine
2,4-di(0,0'-diethylphosphorotrithioyl)-6-(N-methylamino)-1,3,5-triazine
2,4-di(0,0'-diethylphosphorotrithioyl)-6-(N-ethylamino)-1,3,5-triazine
2,4-di(0,0'-diethylphosphorotrithioyl)-6-(N-isopropylamino)-1,3,5-triazine
2,4-di(0,0'-diethylphosphorotrithioyl)-6-(N-butylamino)-1,3,5-triazine
2,4-di(0,0'-diethylphosphorotrithioyl)-6-(N-benzylamino)-1,3,5-triazine
2,4-di(0,0'-diethylphosphorotrithioyl)-6-(N-phenylamino)-1,3,5-triazine
2,4-di(0,0'-diisopropylphosphorotrithioyl)-6-(N-methylamino)-1,3,5-triazine
2,4-di(0,0'-diisopropylphosphorotrithioyl)-6-(N-ethylamino)-1,3,5-triazine
2,4-di(0,0'-diisopropylphosphorotrithioyl)-6-(N-isopropylamino)-1,3,5-triazine
2,4-di(0,0'-diisopropylphosphorotrithioyl)-6-(N-butylamino)-1,3,5-triazine
2,4-di(0,0'-diisopropylphosphorotrithioyl)-6-(N-benzylamino)-1,3,5-triazine
2,4-di(0,0'-diisopropylphosphorotrithioyl)-6-(N-phenylamino)-1,3,5-triazine
2,4-di(0,0'-diisopropylphosphorotrithioyl)-6-amino-1,3,5-triazine and the corresponding phosphorodithioyl compounds. Other examples are:

2-(0,0'-dimethylphosphorotrithioyl)-4,6-di(N,N-dimethylamino)-1,3,5-triazine
2-(0,0'-dimethylphosphorotrithioyl)-4,6-di(N,N-diethylamino)-1,3,5-triazine
2-(0,0'-dimethylphosphorotrithioyl)-4,6-di(N,N-diisopropylamino)-1,3,5-triazine
2-(0,0'-dimethylphosphorotrithioyl)-4,6-di(N,N-dibutylamino)-1,3,5-triazine
2-(0,0'-dimethylphosphorotrithioyl)-4,6-di(N,N-dibenzylamino)-1,3,5-triazine
2-(0,0'-dimethylphosphorotrithioyl)-4,6-di(piperidino)-1,3,5-triazine
2-(0,0'-dimethylphosphorotrithioyl)-4,6-di(2,6-dimethylmorpholino)-1,3,5-triazine
2-(0,0'-dimethylphosphorotrithioyl)-4,6-di(hexahydro-1H-azepin-1-yl)-1,3,5-triazine
2-(0,0'-diisopropylphosphorotrithioyl)-4,6-di(N,N-dimethylamino)-1,3,5-triazine
2-(0,0'-diisopropylphosphorotrithioyl)-4,6-di(N,N-dipropylamino)-1,3,5-triazine
2-(0,0'-diisopropylphosphorotrithioyl)-4,6-di(N,N-dihexylamino)-1,3,5-triazine
2-(0,0'-diisopropylphosphorotrithioyl)-4,6-di(N-ethyl-N-cyclohexylamino)-1,3,5-triazine
2-(0,0'-diisopropylphosphorotrithioyl)-4,6-di(pyrrolidinyl)-1,3,5-triazine
2-(0,0'-diisopropylphosphorotrithioyl)-4,6-di(4-methylpiperidino)-1,3,5-triazine
2-(0,0'-dibenzylphosphorotrithioyl)-4,6-di(N,N-dimethylamino)-1,3,5-triazine
2-(0,0'-dibenzylphosphorotrithioyl)-4,6-di(N,N-diethylamino)-1,3,5-triazine
2-(0,0'-dibenzylphosphorotrithioyl)-4,6-di(N,N-diisopropylamino)-1,3,5-triazine
2-(0,0'-dibenzylphosphorotrithioyl)-4,6-di(N-dicyclohexylamino)-1,3,5-triazine
2-(0,0'-dibenzylphosphorotrithioyl)-4,6-di(morpholino)-1,3,5-triazine
2-(0,0'-dicyclohexylphosphorotrithioyl)-4,6-di(N,N-dimethylamino)-1,3,5-triazine
2-(0,0'-dicyclohexylphosphorotrithioyl)-4,6-di(N,N-dipropylamino)-1,3,5-triazine
2-(0,0'-dicyclohexylphosphorotrithioyl)-4,6-di(N,N-dibutylamino)-1,3,5-triazine
2-(0,0'-dicyclohexylphosphorotrithioyl)-4,6-di(2,5dimethylpyrrolidinyl)-1,3,5-triazine 2-(0,0'-dicyclohexylphosphorotrithioyl)-4,6-di(-dimethylmorpholino)-1,3,5-triazine
2-(0,0'-dicyclohexylphosphorotrithioyl)-4,6-di(N,N-dibenzylamino)-1,3,5-triazine
2-(0,0'-dicyclohexylphosphorotrithioyl)-4,6-di(hexahydro-1(2H) azocin-1-yl)-1,3,5-triazine
2-(0,0'-diethylphosphorotrithioyl)-4,6-di(N,N-dimethylamino)-1,3,5-triazine
2-(0,0'-diethylphosphorotrithioyl)-4,6-di(N,N-dibutylamino)-1,3,5-triazine
2-(0,0'-diethylphosphorotrithioyl)-4,6-di(N-methyl-N-cyclohexylamino)-1,3,5-triazine
2-(0,0'-diethylphosphorotrithioyl)-4,6-di[N,N-di(2-ethylhexylamino)]-1,3,5-triazine
2-(0,0'-diethylphosphorotrithioyl)-4,6-di(N,N-dibenzylamino)-1,3,5-triazine
2-(0,0'-diethylphosphorotrithioyl)-4,6-di(pyrrolidinyl)-1,3,5-triazine
2-(0,0'-diethylphosphorotrithioyl)-4,6-di(-piperidino)-1,3,5-triazine
2-(0,0'-diethylphosphorotrithioyl)-4,6-di(morpholino)-1,3,5-triazine
2-(0-methyl-0'-phenylphosphorotrithioyl)-4,6-di(N,N-dimethylamino)-1,3,5-triazine
2-(0-methyl-0'-phenylphosphorotrithioyl)-4,6-di(N,N-diethylamino)-1,3,5-triazine
2-(0-methyl-0'-phenylphosphorotrithioyl)-4,6-di(N,N-dipropylamino)-1,3,5-triazine
2-(0-methyl-0'-phenylphosphorotrithioyl)-4,6-di(N,N-dibutylamino)-1,3,5-triazine
2-(0-methyl-0'-phenylphosphorotrithioyl)-4,6-di(N,N-dibenzylamino)-1,3,5-triazine
2-(0-methyl-0'-phenylphosphorotrithioyl)-4,6-di(N,N-dicyclohexylamino)-1,3,5-triazine
2-(0,0'-dimethylphosphorotrithioyl)-4,6-di(N-methylamino)-1,3,5-triazine
2-(0,0'-dimethylphosphorotrithioyl)-4,6-di(N-ethylamino)-1,3,5-triazine
2-(0,0'-dimethylphosphorotrithioyl)-4,6-di(N-isopropylamino)-1,3,5-triazine
2-(0,0'-dimethylphosphorotrithioyl)-4,6-di(N-butylamino)-1,3,5-triazine
2-(0,0'-dimethylphosphorotrithioyl)-4,6-di(N-benzylamino)-1,3,5-triazine
2-(0,0'-dimethylphosphorotrithioyl)-4,6-di(N-phenylamino)-1,3,5-triazine
2-(0,0'-diethylphosphorotrithioyl)-4,6-di(N-methylamino)-1,3,5-triazine
2-(0,0'-diethylphosphorotrithioyl)-4,6-di(N-ethylamino)-1,3,5-triazine
2-(0,0'-diethylphosphorotrithioyl)-4,6-di(N-isopropylamino)-1,3,5-triazine
2-(0,0'-diethylphosphorotrithioyl)-4,6-di(N-butylamino)-1,3,5-triazine
2-(0,0'-diethylphosphorotrithioyl)-4,6-di(N-benzylamino)-1,3,5-triazine
2-(0,0'-diethylphosphorotrithioyl)-4,6-di(N-phenylamino)-1,3,5-triazine
2-(0,0'-diisopropylphosphorotrithioyl)-4,6-di(N-methylamino)-1,3,5-triazine
2-(0,0'-diisopropylphosphorotrithioyl)-4,6-di(N-ethylamino)-1,3,5-triazine
2-(0,0'-diisopropylphosphorotrithioyl)-4,6-di(N-isopropylamino)-1,3,5-triazine
2-(0,0'-diisopropylphosphorotrithioyl)-4,6-di(N-butylamino)-1,3,5-triazine
2-(0,0'-diisopropylphosphorotrithioyl)-4,6-di(N-benzylamino)-1,3,5-triazine
2-(0,0'-diisopropylphosphorotrithioyl)-4,6-di(N-phenylamino)-1,3,5-triazine
2-(0,0'-diisopropylphosphorotrithioyl)-4,6-diamino-1,3,5-triazine
and the corresponding phosphorodithioyl compounds. Still others are:
2-(0,0'-diisopropylphosphorotrithioyl)-4-(N-methylamino)-6-(N,N-dimethylamino)-1,3,5-triazine
2-(0,0'-diisopropylphosphorotrithioyl)-4-(N-methylamino)-6-(N,N-diethylamino)-1,3,5-triazine
2-(0,0'-diisopropylphosphorotrithioyl)-4-(N-methylamino)-6-(N,N-dipropylamino)-1,3,5-triazine
2-(0,0'-diisopropylphosphorotrithioyl)-4-(N-methylamino)-6-(N,N-diisopropylamino)-1,3,5-triazine
2-(0,0'-diisopropylphosphorotrithioyl)-4-(N-methylamino)-6-(morpholino)-1,3,5-triazine
2-(0,0'-diisopropylphosphorotrithioyl)-4-(N-methylamino)-6-(piperidino)-1,3,5-triazine
2-(0,0'-diisopropylphosphorotrithioyl)-4-(N-methylamino)-6-(N,N-dimethylamino)-1,3,5-triazine
2-(0,0'-diisopropylphosphorotrithioyl)-4-(N-methylamino)-6-(N,N-diethylamino)-1,3,5-triazine
2-(0,0'-diisopropylphosphorotrithioyl)-4-(N-methylamino)-6-(N,N-dipropylamino)-1,3,5-triazine
2-(0,0'-diisopropylphosphorotrithioyl)-4-(N-methylamino)-6-(N,N-diisopropylamino)-1,3,5-triazine
2-(0,0'-diisopropylphosphorotrithioyl)-4-(N-ethylamino)-6-(morpholino)-1,3,5-triazine
2-(0,0'-diisopropylphosphorotrithioyl)-4-(N-ethylamino)-6-(piperidino)-1,3,5-triazine
2-(0,0'-diisopropylphosphorotrithioyl)-4-(N-dimethylamino)-6-(N,N-diethylamino)-1,3,5-triazine
2-(0,0'-diisopropylphosphorotrithioyl)-4-(N-dimethylamino)-6-(N,N-dipropylamino)-1,3,5-triazine
2-(0,0'-diisopropylphosphorotrithioyl)-4-(N-dimethylamino)-6-(N,N-diisopropylamino)-1,3,5-triazine
2-(0,0'-diisopropylphosphorotrithioyl)-4-(N-dimethylamino)-6-(morpholino)-1,3,5-triazine
2-(0,0'-diisopropylphosphorotrithioyl)-4-(N-dimethylamino)-6-(piperidino)-1,3,5-triazine
and the corresponding phosphorodithioyl compounds.

Examples of tris phosphorodithioyl triazines and chloro diphosphorodithioyl triazines suitable for the practice of this invention are shown in U.S. Pat. No. 2,887,432, the disclosure of which is incorporated herein by reference. A preferred compound is 2,4,6-tris(0,0'-diisopropylphosphorodithioyl)-1,3,5-triazine. The corresponding tris (phosphorotrithioyl) triazines are prepared by reacting three moles of phosphoryl sulfenyl chloride with one mole of 2,4,6-tris-mercapto-1,3,5-triazine in the presence of HCl acceptor. The chloro diphosphoryltrithioyl triazines are prepared by reacting two moles of phosphoryl sulfenyl chloride with 2,4-dimercapto-6-chloro-1,3,5-triazine. Examples of satisfactory tris-disulfides are 2,4,6-tris(0,0'-dimethylphosphorotrithioyl)-1,3,5-triazine, 2,4,6-tris(0,0'-diethylphosphorotrithioyl)-1,3,5-triazine, 2,4,6-tris(0,0'-dipropylphosphorotrithioyl)-1,3,5-triazine, 2,4,6-tris(0,0'-diisopropylphosphorotrithioyl)-1,3,5-triazine, 2,4,6-tris(O,O'-dibutylphosphorotrithioyl)1,3,5-triazine, 2,4,6-tris(O,O'-dibenzylphosphorotrithioyl)-1,3,5-triazine. Examples of suitable 2-phosphorodithioyl-4,6-diamino and 2-phosphorodithioyl-4-amino-6-chloro triazines are shown in British Pat. No. 1,087,029 and *J. Chem. Soc.* 1967, pages 1192–1194, which disclosures are incorporated herein by reference. The corresponding 2-phosphorotrithioyl compounds are prepared by reacting phosphoryl sulfenyl chloride with 2-mercapto-4,6-diamino-1,3,5-triazine or with 2-mercapto-4-amino-6-chloro-1,3,5-triazine. Alternatively, they are prepared by reacting a salt of dithiophosphoric acid with 2-(4,6-diamino)-1,3,5-triazine sulfenyl chloride or with 2-(4-amino-6-chloro)-1,3,5-triazine sulfenyl chloride.

The 2,4-di(phosphorodithioyl)-6-amino-1,3,5-triazines are prepared by reacting two moles of a salt of dithiophosphoric acid with 2,4-dichloro-6-amino-1,3,5-triazine. Examples of suitable 2,4-dichloro-6-amino triazine intermediates are illustrated in *Jour. Am. Chem. Soc.*, 73, pages 2981 and 2984. The 2,4-di(-phosphorotrithioyl)-6-amino-1,3,5-triazines of this invention are prepared by reacting a 6-amino-s-triazine-2,4-disulfenyl chloride with an alkali metal salt or amine salt of a dithiophosphoric acid. The reaction takes place under mild conditions and the product recovered and purified by conventional procedures. However, contrary to conventional order of addition of reactants, it is preferred in the preparation of the compounds of this invention to add the salt of the dithiophosphoric acid to the sulfenyl chloride. The 6-amino-triazinedisulfenyl chloride is prepared by chlorination of the appropriate 6-amino-dimercapto-triazine, examples of which are shown in U.S. Pat. No. 3,366,598.

The nature of the substituents attached to the triazine ring has a pronounced effect upon accelerator activity. For example, phosphorotrithioyl compounds are more potent accelerators than the corresponding phosphorodithioyl compounds. Compounds with dialkylamino substituents exhibit faster cure rates than the corresponding compounds with heterocyclic amino substituents. Compounds with two amino substituents exhibit faster cure rates than compounds with only one amino substituent. Even the nature of the group attached to the oxygen of the phosphoryl moiety effects the properties of the accelerator in rubber. For example, compounds with a secondary or tertiary carbon attached to the oxygen exhibit greater processing safety than compounds with primary carbon attached to the oxygen of the phosphoryl moiety. Thus, it is apparent that accelerators with any desired combination of properties may be tailored by selection of the proper substituents. The di-(phosphorotrithioyl)-mono-amino-triazines are a preferred class of compounds because they possess an excellent balance of properties, namely adequate processing safety, sufficient cure rate and cross-linking efficiency. In addition, vulcanizates containing di(phosphorotrithioyl) triazines exhibit higher moduli than the vulcanizates containing the corresponding di(phosphorodithioyl) triazines which improvement is believed to be the result of the formation of crosslinks in the rubber comprising a bridge consisting of a triazine moiety joined to the rubber molecule through two sulfur atoms attached to two different carbon atoms of the triazine ring. Said mono-sulfidic cross-links are believed to impart the improved reversion resistance exhibited by the vulcanizates vulcanized using di(phosphorotrithioyl) triazines.

The triazine sulfides of this invention are utilized in the same manner as conventional vulcanizing agents and accelerators, namely by incorporation into the rubber compositions and heating to effect vulcanization. The quantity of triazine compound required varies depending upon the properties desired in the vulcanizate. Generally, the quantity of triazine sulfide is greater when used as a vulcanizing agent than when used as an accelerator in combination with sulfur. Amounts of 0.2–10 parts of triazine sulfide per 100 parts rubber are suitable with amounts of 0.5–3.0 parts per 100 parts rubber being the range normally employed. The triazine sulfides of this invention can be used in any sulfur vulcanizable diene rubber. Natural and synthetic rubbers and mixtures thereof are suitable. Synthetic rubbers include cis-4-polybutadiene, butyl rubber, ethylene-propylene terpolymers, polymers of 1,3-butadiene, polymers of isoprene, copolymers of 1,3-butadiene with other monomers, for example, styrene, acrylonitrile, isobutylene, and methylmethacrylate.

The triazine mono- and disulfides are accelerators for the vulcanization of rubber compositions containing sulfur-vulcanizing agents and the disulfides are vulcanizing agents which may be used without other vulcanizing agents being present. Sulfur-vulcanizing agent means elemental sulfur or sulfur containing vulcanizing agent which at cure temperature or below releases sulfur in the form available to cross-link the rubber. Illustrative vulcanizing agents are amine disulfide and polymeric polysulfide, for example, alkyl phenol disulfides and dimorpholinodisulfide. The rubber compositions may contain the usual compounding ingredients, for example, reinforcing pigments such as carbon black or silica, metal oxide activators such as zinc oxide, organic activators such as diphenyl guanidine, stearic acid, antidegradants of the phenolic or amine type, for example, alkylene-bridged cresols, styrenated phenol, sterically-hindered hydroquinones, quinones and N-alkyl-N'phenyl-p-phenylenediamines.

Of course, the triazine sulfides of this invention may be used in combination with conventional accelerators and vulcanizing agents. For certain applications it is sometimes advantageous to employ curative combinations. Examples of conventional materials which may be used in combination with the triazine sulfides of this invention are 2-mercaptobenzothiazole, bis (2-benzothiazolyl) disulfide, N-cyclohexyl-2-benzothiazolesulfenamide, N-tert-butyl-2-benzothiazolesulfenamide, N-diisopropyl-2-benzothiazolesulfenamide, 2-(morpholinothio) benzothiazole, 2(hexahydro-1H-azepin-1-yl) benzothiazole, tetramethylthiuram disulfide, tetraethyl thiuram disulfide, bis(O,O'-diisopropylthiophosphoryl) disulfide, tetramethyl thiuram monosulfide and zinc O,O' di-n-butylphosphorodithioate.

For the rubber stocks tested and described herein as illustrative of the invention, Mooney scorch times are determined by means of a Mooney plastometer. The time in minutes ($t_5$) required for the Mooney reading to rise five points above the minimum viscosity is recorded. Longer times on the Mooney scorch test are desirable because this indicates greater processing safety. Cure characteristics are determined at the designated temperatures by means of the Monsanto Oscillating Disk Rheometer which is described by Decker, Wise and Guerry in *Rubber World*, December, 1962, page 68. From the rheometer data, the maximum torque, R max., in rheometer units is recorded. The increase in torque is a measure of the degree of vulcanization and is proportional to the cross-link density. The time, $t_2$, in minutes for a rise of two rheometer units above the minimum reading of the rubber sample, and the time, $t_{90}$, required to obtain a torque of 90% of the maximum is recorded. The difference, $t_{90}-t_2$, is a measure of the cure rate of the sample. Reversion, a measure of cross-link scission, is determined by observing the decrease in rheometer torque after maximum torque is achieved. Reversion is recorded in rheometer units and is the difference in rheometer maximum torque and rheometer torque 10 minutes after maximum torque is achieved. Vulcanizates are prepared by press curing at the selected temperature for the time indicated by the rheometer data to obtain optimum cure. The physical properties of the vulcanizates are measured by conventional methods.

DESCRIPTION OF PREFERRED EMBODIMENTS

The following illustrate suitable synthesis procedures:

A slurry of cyanuric chloride (92.2g.,0.5 moles) suspended in 200 ml of hot acetone and a solution of morpholine (43.5g,0.5 moles) and sodium carbonate (35.6g,0.34 moles) in 275 ml of water are simultaneously added to 300 ml of water with vigorous stirring. The amount of each reactant added is controlled to maintain the pH between 7 and 8 and the temperature of the reaction mixture is controlled between 0°–5°C. The addition is completed in 30 minutes. After stirring the mixture one hour, a white precipitate is recovered by filtration, washed with water and dried. 2,4-dichloro-6-morpholino-1,3,5-triazine m.p. 150°–153°C is recovered in 75% yield.

A slurry of 2,4-dichloro-6-morpholino-1,3,5-triazine (823g, 0.35 moles) and thiourea (54.8g, 0.72 moles) in 500 ml of methanol were stirred 25 minutes until a solution was obtained (monothiuronium salt formed). The solution is refluxed for 2 hours. A precipitate (dithiuronium salt) formed after about 1 hour. Potassium hydroxide (39.8g,0.71 moles) in 100 ml of water is added in 5 minutes and the mixture is refluxed an additional 30 minutes. The reaction mixture is poured into 1 liter of ice water and the solids recovered by filtration. The product is washed with water and then vacuum dried at 50°C. Fifty seven grams of 2,4-dimercapto-6-morpholino-1,3,5-triazine, m.p. 355°–360°C, is obtained. Chlorination of the dimercapto compound in an inert solvent gives the disulfenyl chloride.

Diisopropyldithiophosphate (44g,0.2 mole) is added at 5°–10°C to a solution of sodium hydroxide (8.0g,0.2 mole) in 300 ml of methanol. 2,4-Dichloro-6-morpholino-1,3,5-triazine (23.5g,0.1 mole) is then added and the reaction mixture refluxed for 3 hours. Sodium chloride by-product is separated by filtration and methanol is stripped from the filtrate on a rotary evaporator. A white solid is recovered which is washed with ether and dried. 2,4-Di(0,0'-diisopropylphosphorodithioyl)-6-morpholino-1,3,5-triazine, 44 grams, m.p. 116°–119°C is obtained.

A solution containing 0.2 moles of diethyldithiophosphate and 0.3 mole of triethylamine in 100 ml of benzene is added in small portions to a stirred solution containing 0.1 mole of 6-morpholino-s-triazine-2,4-disulfenyl chloride in 200 ml of benzene while maintaining the temperature between 20°–25°C. The reaction mixture is stirred for 1 hour at room temperature. The by-product amine salt is separated by filtration and washed with benzene. The benzene filtrate is washed three times with 300 ml portions of water and then dried over sodium sulfate. The benzene is vacuum stripped in a rotary evaporator at 40°C, to give 45.8 grams of an off-white solid. Recrystallization of the crude product gives essentially pure 2,4-di(0,0'-diethylphosphorotrithioyl)-6-morpholino-1,3,5-triazine, m.p. 111°–112°C.

Substituting 0,0'-diisopropyldithiophosphate into the above procedure gives 2,4-di(0,0'-diisopropylphosphorotrithioyl)-6-morpholino-1,3,5-triazine, m.p. 136°–138°C.

A solution containing 0.2 moles of 0,0'-diisopropyldithiophosphate and 0.3 mole of triethylamine in 100 ml of benzene is added in small portions to a stirred solution containing 0.1 mole of 6-diethylamino-s-triazine-2,4-disulfenyl chloride in 200 ml of benzene over a period of 9 minutes at 20°–25°C. After stirring the mixture for 1 hour at room temperature, the by-product amine salt is separated by filtration. The filtrate is washed with water, dried over sodium sulfate and the benzene is evaporated in a rotary evaporator. A yellow oil is obtained which crystallizes upon standing. The solid is washed with methanol and recovered by filtration to give 2,4-di(0,0'-diisopropylphosphorotrithioyl)-6-diethylamino-1,3,5-triazine, m.p. 95°–98°C.

The cure characteristics of the phosphoryl triazine sulfides of this invention are demonstrated in the tables below. A natural rubber masterbatch is prepared by mixing 100 parts natural rubber, 45 parts ISAF carbon black, 30 parts zinc oxide, 2.0 parts stearic acid, 5.0 parts softener and 2.0 parts N-1,3-dimethyl-butyl-N'-phenyl-p-phenylenediamine antidegradant which masterbatch is used to illustrate the invention. To portions of the masterbatch, quantities of phosphoryl triazine sulfide and sulfur are added and the properties of the vulcanizable compositions and vulcanizates determined.

TABLE I

| Stock | 1 | 2 | 3 | 4 | 5 | 6 | 7 |
|---|---|---|---|---|---|---|---|
| Masterbatch | 157.0 ———————————————————→ | | | | | | |
| Sulfur | — | — | — | 1.0 | 1.0 | 1.0 | 1.0 |
| 2,4-di(0,0'-diethyl-phosphorotrithioyl-6-morpholino-1,3,5-triazine | 3.0 | — | — | 1.0 | — | — | — |
| 2,4-di(0,0'-diisopropyl-phosphorotrithioyl)-6-(N,N-diethylamino)-1,3,5-triazine | — | 3.0 | — | — | 1.0 | — | — |
| 2,4-di(0,0'-diisopropyl-phosphorotrithioyl)-6-morpholino-1,3,5-triazine | — | — | 3.0 | — | — | 1.0 | — |
| 2-(0,0'-diisopropyl-phosphorotrithioyl)4,6-di-(N,N diethylamino)-1,3,5- | | | | | | | 1.0 |

TABLE I-continued

| Stock | 1 | 2 | 3 | 4 | 5 | 6 | 7 |
|---|---|---|---|---|---|---|---|
| triazine | | | | | | | |
| Mooney Scorch at 250°F | | | | | | | |
| $t_s$ | 42.0 | 97.0 | 103.4 | 32.4 | 45.8 | 46.0 | 12.7 |
| Rheometer Data at 292°F | | | | | | | |
| $t_{90}-t_2$ | 47.7 | 52.8 | 75.8 | 11.2 | 16.1 | 11.1 | 4.8 |
| R max. | 45.8 | 40.0 | 37.5 | 52.2 | 61.1 | 52.1 | 52.8 |
| Stress-Strain at 292°F | | | | | | | |
| Cure time, minutes | 90 | 120 | 120 | 35 | 60 | 30 | 15 |
| 300% Modulus, psi | 1040 | 880 | 880 | 1120 | 1470 | 1120 | 1100 |
| Ult. tensile, psi | 3390 | 3230 | 3020 | 3620 | 3950 | 3840 | 3710 |
| Rheometer Data at 328°F | | | | | | | |
| $t_{90}-t_2$ | 7.9 | 12.0 | 13.8 | 2.5 | 3.1 | 3.1 | 2.2 |
| R. max. | 42.9 | 38.1 | 38.3 | 48.1 | 52.2 | 48.2 | 46.5 |
| Reversion | 0.5 | 0.1 | 0.4 | 3.3 | 0.9 | 1.8 | 3.4 |

The data show that the triazine disulfides of this invention are vulcanizing agents when used alone and that they are delayed-action fast curing accelerators when used with sulfur. The effect of the substituents upon cure characteristics is pronounced. For example, the presence of a secondary alkyl group on the phosphoric acid moiety enhances the processing safety significantly when the triazine disulfide is used either as a vulcanizing agent or as an accelerator. (Compare Stocks 1 vs 3 and 4 vs 6). When used as an accelerator, the triazine compound having a dialkylamino substituent is a more potent accelerator than the corresponding triazine compound having an heterocyclicamino substituent. (Compare Stocks 5 and 6). An accelerator with two amino substituents in the triazine ring (Stock 7) enhances the cure rate but reduces the processing safety of the composition.

TABLE II

| Stock | 1 | 2 | 3 | 4 |
|---|---|---|---|---|
| Masterbatch | 157.0 ————————————→ | | | |
| Sulfur | — | — | 1.0 | 1.0 |
| 2,4-di(0,0'-diethylphosphorotrithioyl)-6-morpholino-1,3,5-triazine | 3.0 | — | 1.0 | — |
| 2,4-di(2-benzothiazolyldithio)-6-morpholino-1,3,5-triazine | — | 3.0 | — | 1.0 |
| Mooney Scorch at 250°F | | | | |
| $t_s$, minutes | 46.0 | 41.3 | 37.1 | 29.6 |
| Rheometer Data at 292°F | | | | |
| $t_{90}-t_2$ | 28.9 | 55.9 | 12.4 | 16.1 |
| R. max. | 57.0 | 48.8 | 51.3 | 51.0 |
| Stress-Strain at 292°F | | | | |
| Cure time, minutes | 55 | 95 | 35 | 40 |
| 300% modulus, psi | 1340 | 970 | 1100 | 980 |
| Ult. tensile, psi | 3490 | 3310 | 3320 | 2910 |
| Rheometer at 328°F | | | | |
| $t_{90}-t_2$ | 6.1 | 12.8 | 2.9 | 4.0 |
| R. max. | 49.7 | 43.2 | 49.0 | 46.3 |
| Reversion | 0.6 | 1.5 | 3.0 | 3.7 |

The data of Table II compares the cure characteristics of a triazine disulfide of this invention with the corresponding benzothiazolyl triazine disulfide which is a known vulcanizing agent and rubber accelerator, Westlinning et. al. U.S. Pat. No. 3,366,598. The data show that the dithiophosphoric acid compound of this invention is superior in several respects; for example, it possesses greater processing safety and exhibits a faster rate of cure. In addition, it produces vulcanizates having higher modulus and tensile strengths and which vulcanizates exhibit improved reversion resistance.

TABLE III

| Stock | 1 | 2 | 3 | 4 |
|---|---|---|---|---|
| Masterbatch | 157.0 ————————————→ | | | |
| Sulfur | 2.0 | 2.0 | — | — |
| 2,4-di(0,0'-diisopropyl-phosphorotrithioyl)-6-morpholino-1,3,5-triazine | 0.5 | — | 3.0 | — |
| 2,4-di(0,0'-diisopropyl-phosphorodithioyl)-6-morpholino-1,3,5-triazine | — | 0.5 | — | 3.0 |
| Mooney Scorch at 250°F | | | | |
| $t_s$, minutes | 28.6 | 64.6 | 81.2 | — |
| Rheometer Data at 292°F | | | | |
| $t_{90}-t_2$ | 16.5 | 47.5 | 82.4 | No cure |
| R. max. | 48.0 | 26.2 | 42.8 | — |
| Stress-Strain at 292°F | | | | |
| Cure time, minutes | 40 | 120 | 120 | — |
| 300% modulus, psi | 1230 | 790 | 1200 | — |
| Ult. tensile, psi | 3680 | 1980 | 3670 | — |
| Rheometer Data at 328°F | | | | |
| $t_{90}-t_2$ | 4.5 | 14.0 | 15.7 | — |
| R. max. | 45.7 | 30.1 | 41.6 | — |
| Reversion | 4.7 | 1.5 | 0.2 | — |

The vulcanization characteristics of mono-sulfide and disulfide triazines are compared in Table III. The monosulfide compound has greater processing safety but the disulfide compound is a more efficient accelerator which cures faster and produces higher modulus vulcanizates. The disulfide is a vulcanizing agent whereas the monosulfide is ineffective when used alone.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formula

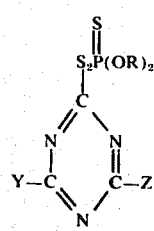

in which Y is

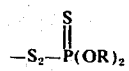

or

and Z is

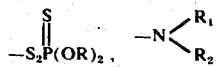

or Cl in which each R independently is alkyl of 1–8 carbon atoms, cycloalkyl of 5–8 carbon atoms, benzyl, phenyl or tolyl, and $R_1$ and $R_2$ independently are hydrogen, alkyl of 1–8 carbon atoms, cycloalkyl of 5–8 carbon atoms, benzyl, phenyl or tolyl or

is a heterocyclic radical selected from the group consisting of pyrrolidinyl, 2,5-dimethylpyrrolidinyl, piperidino, 4-methylpiperidino, morpholino, thiomorpholino, 2,6-dimethylmorpholino, hexahydro-1H-azepin-1-yl, hexahydro-1(2H)-azocin-1-yl, and azabicyclo(3.2.2)-non-3-yl.

2. A compound of claim 1 in which Y and Z are

3. A compound of claim 2 in which $R_1$ and $R_2$ are ethyl and R is isopropyl.

4. A compound of claim 1 in which Y is

and Z is

5. A compound of claim 4 in which $R_1$ and $R_2$ are lower alkyl.

6. A compound of claim 5 in which $R_1$ and $R_2$ are ethyl.

7. A compound of claim 6 in which R is isopropyl.

8. A compound of claim 4 in which

is an heterocyclic radical.

9. A compound of claim 8 in which R is isopropyl.

10. A compound of claim 9 in which

is morpholino.

* * * * *